United States Patent
Koumenis et al.

(10) Patent No.: US 6,689,811 B2
(45) Date of Patent: Feb. 10, 2004

(54) METHOD OF USING CAFFEIC ACID PHENETHYL ESTER AND ANALOGS THEREOF AS RADIATION SENSITIZERS

(75) Inventors: Constantinos Koumenis, Winston-Salem, NC (US); Christine Naczki, Winston-Salem, NC (US)

(73) Assignee: Wake Forest University, Winston-Salem, NC (US)

( * ) Notice: Subject to any disclaimer, the term of this patent is extended or adjusted under 35 U.S.C. 154(b) by 0 days.

(21) Appl. No.: 10/126,445

(22) Filed: Apr. 19, 2002

(65) Prior Publication Data

US 2002/0188021 A1 Dec. 12, 2002

Related U.S. Application Data

(60) Provisional application No. 60/285,317, filed on Apr. 20, 2001.

(51) Int. Cl.[7] .............................................. A61K 31/235
(52) U.S. Cl. ......................... 514/532; 514/533; 514/544
(58) Field of Search .................................. 514/532, 533, 514/544

(56) References Cited

U.S. PATENT DOCUMENTS

| | | | | |
|---|---|---|---|---|
| 5,008,441 A | * | 4/1991 | Nakanishi et al. | 560/75 |
| 5,981,583 A | * | 11/1999 | Aggarwal et al. | 514/532 |
| 6,251,644 B1 | * | 6/2001 | Sowemimo-Coker et al. | 435/173.3 |
| 6,313,165 B1 | * | 11/2001 | Grunberger et al. | 514/532 |

* cited by examiner

*Primary Examiner*—James H Reamer
(74) *Attorney, Agent, or Firm*—Myers Bigel Sibley & Sajovec, PA

(57) ABSTRACT

A method of potentiating radiation therapy in a subject in need thereof comprises administering a potentiating agent such as caffeic acid phenethyl ester (CAPE) or an analog thereof to the subject in an amount effective to potentiate radiation therapy in the subject.

19 Claims, 7 Drawing Sheets

METHOD OF USING CAFFEIC ACID PHENETHYL ESTER AND ANALOGS THEREOF AS RADIATION SENSITIZERS

CROSS REFERENCE TO RELATED APPLICATION

The present application claims priority to U.S. Provisional Application No. 60/285,317, filed Apr. 20, 2001, the disclosure of which is incorporated herein by reference in its entirety.

FIELD OF THE INVENTION present invention concerns the use of caffeic acid phenethyl esters as radiation sensitizers in the treatment of tumors in subjects in need thereof.

BACKGROUND OF THE INVENTION

Adenocarcinoma of the prostate is the most commonly diagnosed non-skin cancer and the second leading cause of cancer deaths in the United States (F. Keely and L. Gomella, *Epidemiology of Prostate Cancer*, in *Prostate Cancer*, M. Ernstoff, J. Heany, and R. Peschel, Eds., 1998, p.2–14). Currently, the only therapies that have shown significant promise for curability of localized disease are radical prostatectomy and radiation therapy (RT). Selection of each type of treatment depends mainly upon tumor stage, with the majority of patients with A2 and B1 tumors receiving surgery, while those with stages B2, or C and higher-grade tumors are treated with radiation (R. Peschel, *External Beam Radiation Therapy for Local Prostate Cancer*, in *Prostate Cancer*, p. 117–136).

Studies have suggested that adjuvant radiotherapy following prostatectomy provides superior results in terms of biochemical relapse (Prostate Specific Antigen levels) than surgery alone (R. Peschel, supra). Radiation therapy can consist of Conventional External Beam Radiotherapy, Three-Dimensional Conformal Radiation Therapy, or Radioactive Implant therapy. The latter modality, which was first developed in the early 1970's and is currently experiencing a resurgence, offers the advantage of delivery of relatively high-dose radiation therapy in a localized area. Despite the effectiveness of these different RT modalities in achieving local control of the disease and reducing the mortality rate of prostate cancer patients, approximately 20–40% of patients with local disease receiving irradiation will relapse at the site of irradiation (P. Scardino and T. Wheeler, *NCI Monogr*, 7, 95–103 (1988); J. Crook et al., *Urology* 45, 624–31 (1995); J. Crook et al., *Cancer* 79, 81–9 (1997)).

Moreover, studies have shown that cells that survive initial irradiation treatments are the ones most likely to form clones that will eventually repopulate the irradiated area and potentially metastasize (Z. Fuks et al., *Int. J. Radiat. Oncol. Biol. Phys.* 21, 537–547 (1991)). Thus, new combined modalities using agents that increase the lethal effects of ionizing radiation have the potential of reducing the probability of tumor recurrence and to increase disease-free survival times in patients treated with RT. Though a number of such agents have been shown to be effective in sensitizing prostate tumor cells to Ionizing Radiation (IR) in vitro, these results have not yet translated into effective combined modalities in the clinic, either because of lack of effectiveness in vivo, or because of potential toxicity or unknown long-term effects of such agents (M. Garzotto et al., *Cancer Res.* 59, 5194–201 (1999); K. Kimura et al., *Cancer Res.* 59, 1606–14 (1999)). Accordingly, there is a need for new ways to potentiate the activity of ionizing radiation in therapies for the treatment of cancers such as prostate cancer.

SUMMARY OF THE INVENTION

A first aspect of the present invention is a method of potentiating radiation therapy in a subject in need thereof, comprising administering caffeic acid phenethyl ester (CAPE) or an analog thereof (a potentiating agent or active compound) to said subject in an amount effective to potentiate radiation therapy in said subject. By "potentiating radiation therapy" is meant increasing or enhancing (e.g., synergistically enhancing) the activity of radiation therapy on a tumor in said subject.

A second aspect of the present invention is a method of treating a tumor in said subject, comprising concurrently administering a potentiating agent as described above (i.e., CAPE or an analog thereof) to said subject while also administering radiation therapy (e.g., ionizing radiation) to said tumor, the potentiating agent being administered to said subject in an amount effective to potentiate the activity or efficacy of the radiation therapy (e.g., by increasing or enhancing, particularly synergistically enhancing) the activity of the radiation therapy on said subject).

A third aspect of the present invention is a method of potentiating antineoplastic therapy in a subject in need thereof, comprising administering caffeic acid phenethyl ester (CAPE) or an analog thereof (a potentiating agent) to said subject in an amount effective to potentiate antineoplastic therapy in said subject. By "potentiating antineoplastic therapy" is meant increasing or enhancing (e.g., synergistically enhancing) the activity of an antineoplastic agent administered to said subject on a tumor in said subject.

A fourth aspect of the present invention is a method of treating a tumor in said subject, comprising concurrently administering a potentiating agent as described above (i.e., CAPE or an analog thereof) to said subject while also an antineoplastic agent to said subject, the potentiating agent being administered to said subject in an amount effective to potentiate the activity or efficacy of the antineoplastic agent (e.g., by increasing or enhancing, particularly synergistically enhancing) the activity of antineoplastic agent on a tumor in said subject).

A further aspect of the present invention is a composition for treating a tumor in a subject, comprising, in combination in a pharmaceutically acceptable carrier, (i) a potentiating agent comprising CAPE or an analog thereof, and (ii) an antineoplastic agent. The potentiating agent is included in the composition in an amount effective to potentiate the activity of the antineoplastic agent.

A still further aspect of the present invention is the use of an active compound as described above for the preparation of a medicament for the treatment of a disorder as described above, or carrying out a method as described above.

The present invention is explained in greater detail in the specification set forth below and the drawings herein.

DETAILED DESCRIPTION OF PREFERRED EMBODIMENTS

Figure 1A:
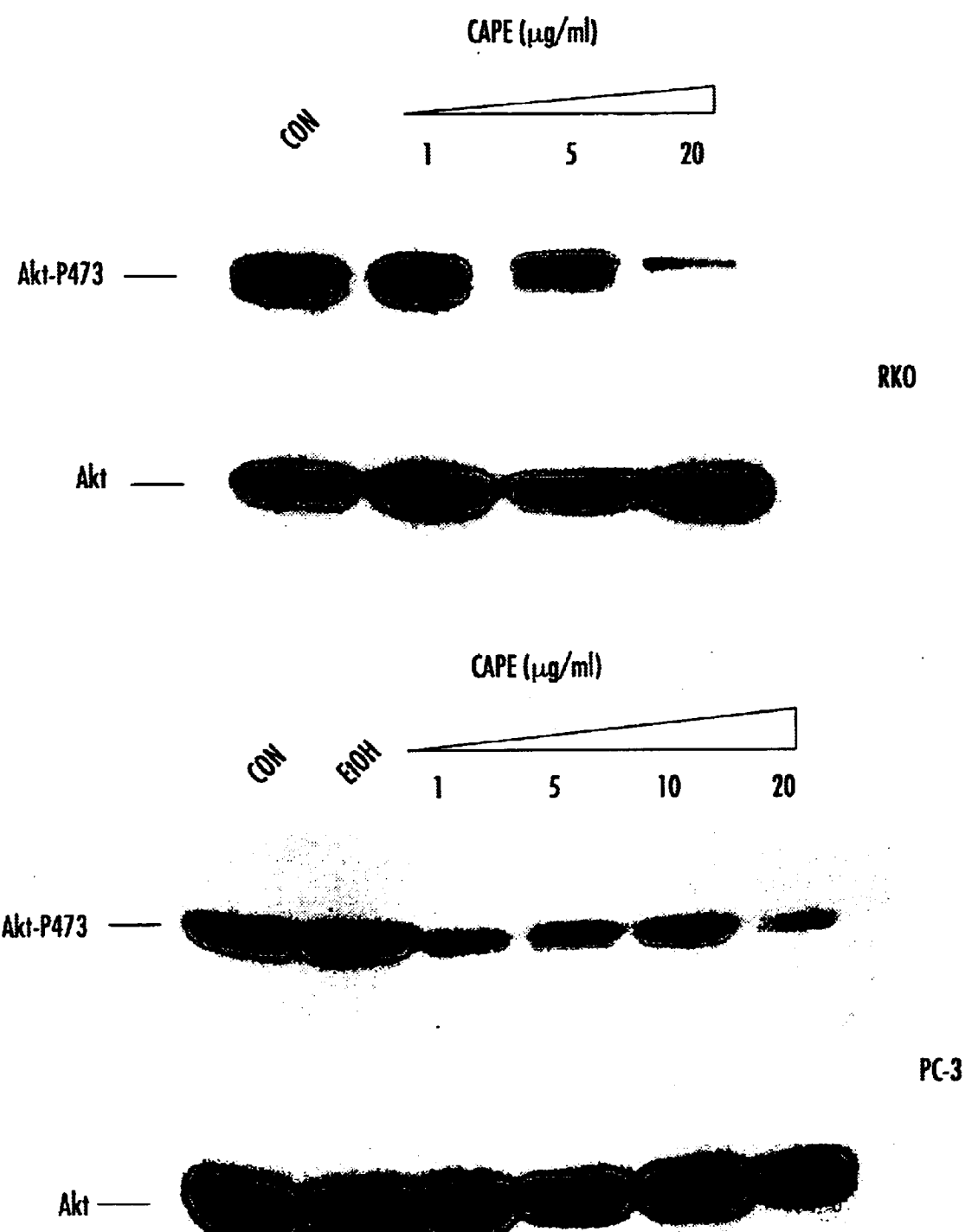
FIG. 1A shows the treatment of RKO cells (top) and PC-3 cells (bottom) with increasing doses of CAPE reduces the levels of Akt phosphorylation (Akt-Pser473). Immunoblotting with an anti-Akt antibody demonstrates that the levels of Akt remain unchanged by CAPE.

The present invention is primarily concerned with the treatment of human subjects, but the invention may also be carried out on animal subjects, particularly mammalian subjects such as mice, rats, dogs, cats, rabbits, livestock and horses, for veterinary purposes, and for drug screening and drug development purposes.

The term "treat" as used herein refers to any type of treatment that imparts a benefit to a patient or subject afflicted with a disease, including improvement in the condition of the patient (e.g., in one or more symptoms), delay in the progression of the disease, etc.

By "potentiating" is meant an increase in the beneficial activity or efficacy of the radiation therapy over that which would be expected from the radiation therapy alone, the potentiating agent alone, or the sum of the activity of the radiation therapy when administered alone and the potentiating agent when administered alone.

Patients or subjects treated by the method of the present invention are generally those afflicted with a tumor (particularly a solid tumor), which may be cancerous. These teams may include tumors in the lung, breast, colon, prostate, liver, ovary, stomach, mouth or brain. The present invention may be used to treat a prostate tumor or cancer, such as adenocarcinoma of the prostate, including stage B2, C, or higher grade tumors.

As used herein, the administration of two or more compounds or treatments (e.g., a potentiating agent and radiation treatment) concurrently or "in combination" means that the two are administered closely enough in time that the presence of one alters the biological effects of the other. The two may be administered simultaneously or sequentially. Simultaneous administration may be carried out by mixing compounds prior to administration, or by administering the compounds or treatment at the same point in time but at different anatomic sites or using different routes of administration. For example, the active compounds described herein may be administered orally or parenterally to a patient prior to receiving radiation therapy.

The term "pharmaceutically acceptable" as used herein means that the compound or composition is suitable for administration to a subject to achieve the treatments described herein, without unduly deleterious side effects in light of the severity of the disease and necessity of the treatment.

Applicants specifically intend that the disclosures of all United States patent references cited herein be incorporated herein by reference.

1. Active Compounds.

Active compounds (potentiating agents) that may be used to carry out the present invention include CAPE and analogs (e.g., derivatives) thereof. Such compounds are known and disclosed in, for example, U.S. Pat. No. 5,981,583 to Aggarwal et al.; U.S. Pat. No. 5,591,773 to Grunberger et al.; and U.S. Pat. No. 5,008,441 to Nakanishi et al. Compounds which may be used to carry out the present invention include such compounds as those having the general structure of Formula 1:

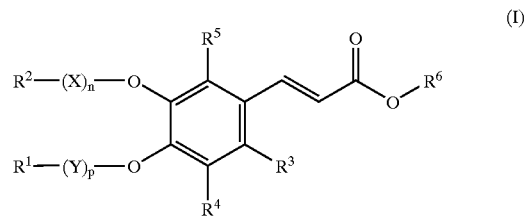

(I)

wherein:
X and Y are independently carbonyl, C=S, S=O, or O=S=O;

n and p are independently 0 or 1;

$R^1$ and $R^2$ are independently hydrogen, linear or branched $C_1$–$C_{18}$ alkyl, alkenyl, or alkynyl, either unsubstituted or substituted with halogen, including F, Cl, Br, and I, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$ are independently hydrogen, halogen, including F, Cl, Br, and I, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S) $R^{14}$, (S=O) $R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, including, F, Cl, Br, and I, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl; or a pharmaceutically acceptable salt thereof.

As used herein, the phrase "halo" in the terms "haloalkyl" and "trihalomethyl" is intended to mean F, Cl, Br, or I.

Methods of synthesizing caffeic acid esters which may be used to synthesize compounds having the above-defined structure have been disclosed in Nakanishi et al., U.S. Pat. No. 5,008,441. Further examples of the above-defined compound can be readily synthesized by one of ordinary skill in the art based on the disclosure of U.S. Pat. No. 5,008,441 and using techniques generally known to those of ordinary skill. Examples of such methods include the general organic synthesis techniques disclosed in such texts as March, J. Advanced Organic Chemistry, 3rd ed. (Wiley; N.Y.: 1985), the contents of which are hereby incorporated by reference.

In a preferred embodiment, n and p are 0, and $R_1$, $R_2$, $R_3$, $R_4$, and $R_5$ are hydrogen. In another preferred embodiment, n and p are 0; $R_1$, $R_2$, $R_3$, $R_4$, and $R_5$ are hydrogen; and $R_6$ is hexyl, butyl, ethyl, or phenylethyl.

In a particular embodiment, the active compound is CAPE and has the structure:

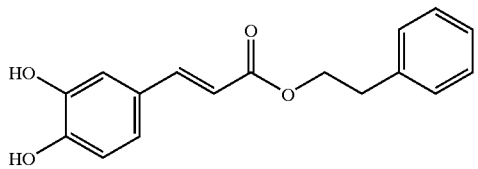

Active compounds of the invention are preferably caffeic acid esters that are inhibitors of Akt phosphorylation.

Active compounds of the present invention may optionally be administered in conjunction with other compounds useful in the treatment of tumors or cancer, such as the antineoplastic agents described below. The other compounds may optionally be administered concurrently with the active compounds above and the radiation therapy.

The active compounds disclosed herein can, as noted above, be prepared and administered in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, The Science And Practice of Pharmacy ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound, or salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10, 50 or 100 mg to about 10, 20 or 50 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active compound potentiating agent.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method including, but not limited to, the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

In addition to active compounds or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 1, 10 or 50 $\mu$g/kg to about 200, 500 or 1,000 $\mu$g/kg are preferred, with particular dosages depending upon the age, weight and condition of the subject, route of administration, type and severity of disease, type or types of concurrent therapy, etc.

4. Radiation Treatment.

The active compounds of present invention can be used as potentiating agents for any type of radiation therapy (e.g., ionizing radiation therapy) in which radiation is administered to the site of the tumor, or a tumor, in the subject. Radiation therapy may be carried out by any suitable technique, including brachytherapy (see, e.g., U.S. Pat. No. 6,196,963) and teletherapy. In particular examples, radiation therapy may be carried out by directing gamma rays or beams, roentgen rays or beams, or electron beams at the tumor. Suitable techniques include conventional external beam radiotherapy, three-dimensional conformal radiation therapy, radioactive implant therapy (such as implantation of radioactive beads, particles or seeds), etc. Radioisotopes may be administered parenterally to the subject, such as by injection of an antibody specific to the tumor, which antibody is conjugated to a radioisotope. Examples of suitable radioisotopes for implantation include but are not limited to those described in U.S. Pat. No. 6,214,315 at column 7. Dosage of the radiation may be determined in accordance with known techniques depending upon the particular radiation therapy employed.

Additionally, a radiation sensitizing agent may be used. This radiation sensitizing agent may enhance the effectiveness of radiation therapy. The agent may accumulate within the tumor, and then can be traced on a MRI to help radiation oncologists more precisely focus the radiation beam. By fine tuning the focus of radiation it may allow a health provider to more effectively destroy the tumor, while limiting damage to the surrounding healthy tissue. Radiation sensitizing agents include, but are nor limited to, implanted neural stem cells that are genetically altered to express a radiation sensitizing agent, taxols such as paclitaxel, various texaphyrins, carious camptothecins such as 9-amino-20(S)-camptothecin, etc. Examples of camptothecin analogs that can be used to carry out the present invention include, but are not limited to, those described in U.S. Pat. No. 4,894,456 to Wall et al.; U.S. Pat. No. 4,399,282 to Miyasaka, et al.; U.S. Pat. No. 4,399,276 to Miyasaka, et al.; U.S. Pat. No. 4,943,579 to Vishnuvajjala, et al.; European Patent Application 0 321 122 A2; U.S. Pat. No. 4,473,692 to Miyasaka, et al. European Patent application No. 0 325 247 A2; European Patent application 0 556 585 A2 filed by Takeda Chemical Industries; U.S. Pat. No. 4,981,968 to Wall, et al.; U.S. Pat. No. 5,049,668 to Wall, et al.; U.S. Pat. No. 5,162,532 to Comins, et al.; U.S. Pat. No. 5,180,722 to Wall, et al; U.S. Pat. No. 5,200,524 to Comins, et al.; U.S. Pat. No. 5,459,269 to Comins, et al.; U.S. Pat. No. 5,162,532 to Fang et al.; and U.S. Pat. No. 6,328,953 to Angelucci et al. (the disclosures of all patent references cited herein are incorporated by reference in their entirety). Examples of taxoid groups that can be used to carry out the present invention include, but are not limited to, those described in U.S. Pat. No. 5,614,645 to Kingston et al.; U.S. Pat. No. 6,028,206 to Chattopadhyay et al; U.S. Pat. No. 5,411,984 to Kingston et al.; and U.S. Pat. No. 5,508,447 to Magnus (the disclosures of all patent references cited herein are incorporated by reference in their entirety).

5. Antineoplastic Agents.

As noted above, the active compounds of the present invention can also be used as potentiating agents for antineoplastic agents. Example antineoplastic agents for use in the present invention include, but are not limited to, vinca alkaloids, epipodophyllotoxins, anthracycline antibiotics, actinomycin D, plicamycin, puromycin, gramicidin D, taxol, colchicine, cytochalasin B, emetine, maytansine, and amsacrine (or "mAMSA"). Preferred are vinca alkaloids, epipodophyllotoxins, anthracyclene antibiotics, actinomycin D, oxaliplatin and plicamycin.

The vinca alkaloid class is described in Goodman and Gilman's, "The Pharmacological Basis of Therapeutics", 1277–1280 (7th ed. 1985) (hereafter "Goodman and Gilman"). Exemplary of vinca alkaloids are vincristine, vinblastine, and vindesine.

The epipodophyllotoxin class is described in Goodman and Gilman, supra at 1280–1281. Exemplary of epipodophyllotoxins are etoposide, etoposide orthoquinone, and teniposide.

The anthracycline antibiotic class is described in Goodman and Gilman, supra at 1283–1285. Exemplary of anthracycline antibiotics are daunorubicin, doxorubicin, mitoxantraone, and bisanthrene. Daunorubicin and doxorubicin are preferred.

Actinomycin D, also called Dactinomycin, is described in Goodman and Gilman, supra at 1281–1283. Plicamycin, also called mithramycin, is described in Goodman and Gilman, supra at 1287–1288.

Additional examples of antineoplastic agents include, but are not limited to, cisplatin, camptothecin, paclitaxel, Ara-C, gemcitabine, etc (including pharmaceutically acceptable salts thereof).

Antineoplastic agents as described above may be administered in their known dosages and in accordance with known techniques, including the techniques described above with respect to the potentiating agents.

In addition to use in combination with the potentiating agents alone, antineoplastic agents as described herein may be administered concurrently with both the active compounds herein and radiation therapy as described above.

The present invention is explained in greater detail in the following non-limiting Examples.

EXAMPLE 1

Treatment of RKO Cells and PC-3 Cells with CAPE

Because of the similarity of in vivo biological activity between synthetic COX-2 inhibitors and the demonstrated ability of plant phenolic antioxidants to inhibit kinase activity in vitro, we hypothesized that these compounds could also be affecting Akt phosphorylation (M. Weyant et al., Cancer Res. 6, 949–56 (2000); A. Hsu et al., J. Biol. Chem. 275, 11397–403 (2000)). The recent finding that Akt phosphorylates the inhibitory subunit of NF-KB, IkB and thus activates NF-kB activity further suggested that Akt phosphorylation might be a target for CAPE (O. Ozes et al., Nature, 1999. 401(6748): p. 82–5; Kane, L. P., et al., Curr Biol, 1999. 9(11): p. 601–4; Romashkova, J. A. and S. S. Makarov, Nature, 1999. 401(6748): p. 86–90; Datta, S. R., A. Brunet, and M. E. Greenberg, Genes Dev, 1999. 13(22): p. 2905–27). Indeed, CAPE was found to be a potent inhibitor of Akt phosphorylation in colorectal carcinoma and prostate tumor cells at doses that it induces apoptosis and radiosensitization (FIG. 1A). This is the first demonstration of a naturally occurring compound inhibiting Akt phosphorylation and raises the possibility that other agents with similar structure will also affect the activity of this important molecule. The tumor suppressor PTEN, which downregulates the activity of Akt by decreasing its phosphorylation levels, was found to be mutated in both localized and metastatic sporadic prostate cancer (Li, J., et al., Science, 1997. 275(5308): p. 1943–7; Cairns, P., et al., Cancer Res, 1997. 57(22): p. 4997–5000; Suzuki, H., et al., Cancer Res, 1998. 58(2): p. 204–9; Feilotter, H. E., et al., Oncogene, 1998. 16(13): p. 1743–8; Whang, Y. E., et al., Proc Natl Acad Sci USA, 1998. 95(9): p. 5246–50; Vlietstra, R. J., et al., Cancer Res, 1998. 58(13): p. 2720–3; Facher, E. A. and J. C. Law, J Med Genet, 1998. 35(9): p. 790; Giri, D. and M. Ittmann, Hum Pathol, 1999. 30(4): p. 419–24; Davies, M. A., et al., Cancer Res, 1999. 59(11): p. 2551–6). Since PTEN is mutated in PC-3 cells, Akt phosphorylation levels are elevated compared to normal prostatic cells, and therefore PC-3 cells are a good model to study the regulation of Akt by CAPE and propolis.

Figure 1B:
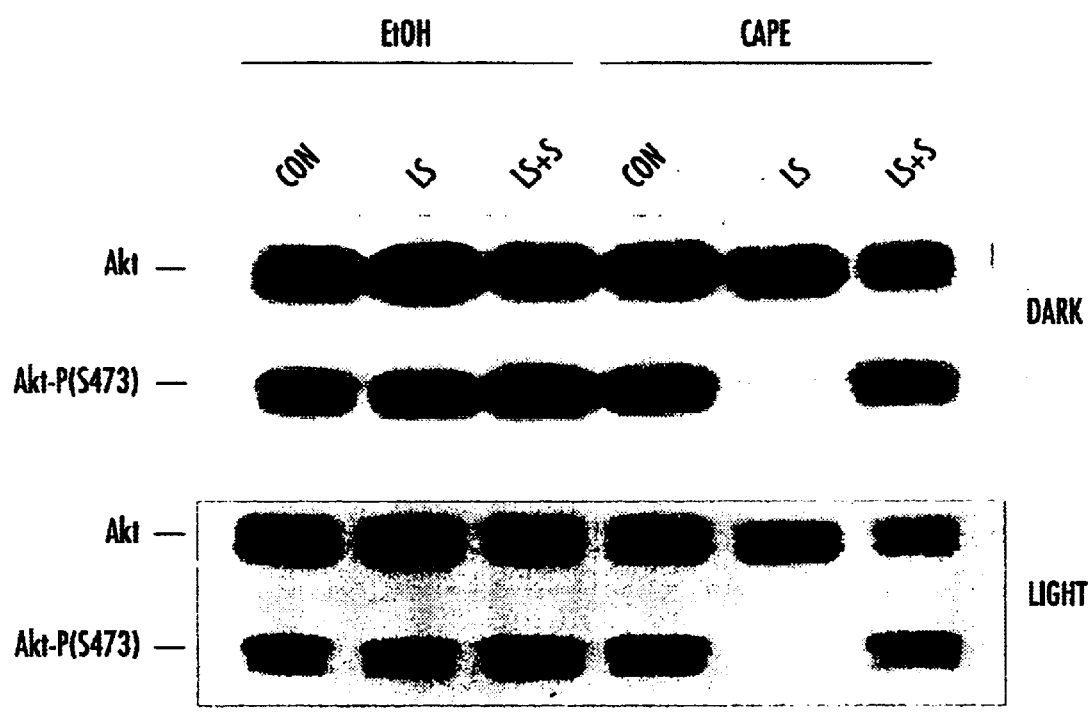
FIG. 1B show another gel in which CAPE synergizes with low serum to reduce Akt phosphorylation levels, but does not prevent re-phosphorylation of Akt upon serum addition. RKO cells were treated with low serum (LS) (0.1%) for 12 h, or low serum for 12 h followed by replacement of media with 10% serum (LS+S), in the absence (EtOH) or presence of CAPE. Two different exposures (light, dark) of the immunoblot using the anti-phosphoAkt specific antibody are shown.

Since Akt phosphorylation levels reflect a balance between active phosphorylation (mainly by PI-3 kinase) and dephosphorylation (by a yet unidentified phosphatase), the decrease in Akt phosphorylation could be an activation of a phosphatase rather than inhibition of a kinase. Akt phosphorylation is upregulated by a number of growth factors found in serum (Takata, M., et al., J Biol Chem, 1999. 274(29): p. 20611–8; Zheng, W. H., S. Kar, and R. Quirion, J Biol Chem, 2000; Jung, F., et al., Cardiovasc Res, 2000. 48(1): p. 148–57). Thus, we performed CAPE treatments in the presence of high (10%) and low (0.1%) serum levels. As shown in FIG. 1B, serum acted synergistically with CAPE to reduce Akt phosphorylation to undetectable levels. However, the presence of CAPE did not inhibit rephosphorylation of Akt when serum was added back to the media. These results suggest that CAPE slowly reduces Akt phosphorylation by inducing a phosphatase activity, rather than by inhibiting an Akt kinase.

EXAMPLES 2–3

Potentiation of Ionizing Radiation with CAPE

Figure 2A:
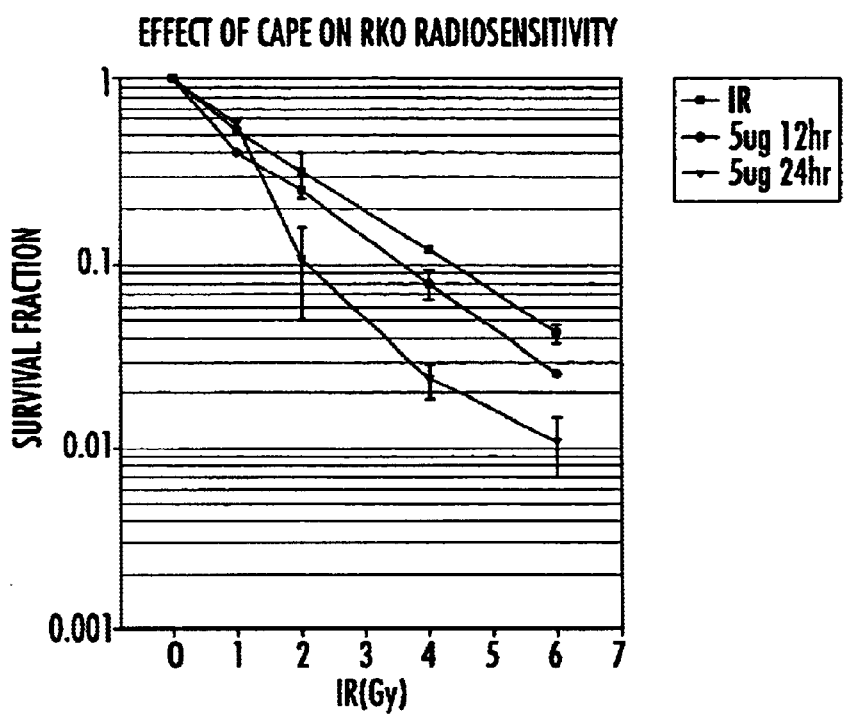
FIGS. 2A–B are graphs illustrating that CAPE sensitizes colorectal carcinoma cells RKO (A) and HT-29 cells (B) to treatments with IR. RKO (A) and HT-29 (B) cells were treated with CAPE (5 µg/ml) for the indicated times, irradiated and plated for clonogenic survival assays. CAPE treatment alone induced 10–20% reduction in clonogenic survival. Results are normalized to account for this reduction.
Figure 2B:
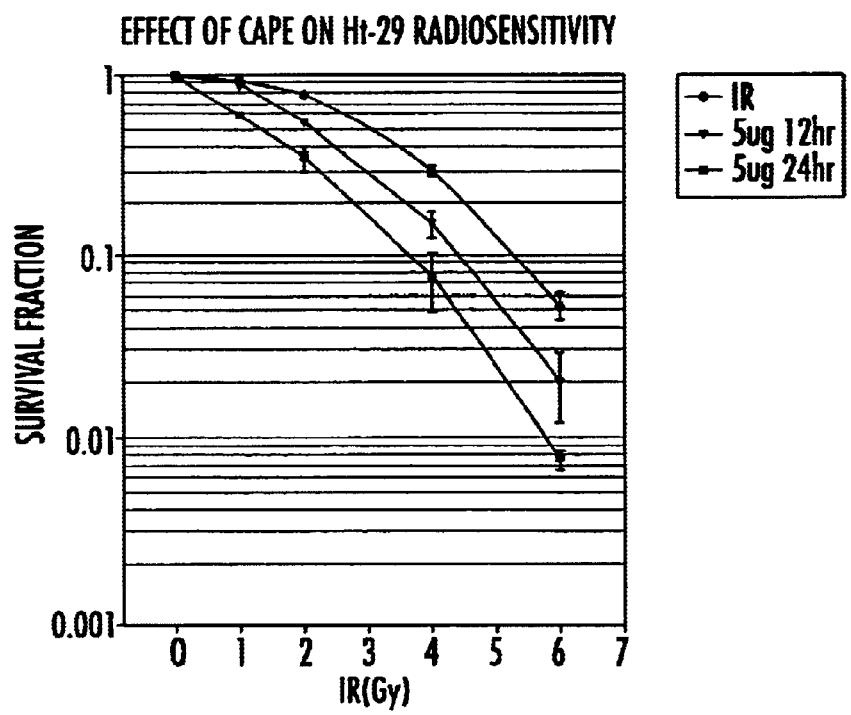

We have also tested the ability of CAPE to sensitize cells to the cytotoxic effects of ionizing radiation. CAPE has demonstrated significant radioenhancing properties in vitro and in vivo in xenograft tumor models. As shown in FIGS. 2A–B, pretreatment of colorectal carcinoma cells with CAPE for 12 h or 24 h resulted in a significant sensitization to IR treatments. The Dose-enhancement ratio (DER) values at survival fraction (SF) 0.1 for pretreatment with CAPE for 24 h were 1.81 for RKO cells and a 1.68 for HT-29 cells. The radiosensitizing effect of CAPE was even more pronounced in vivo.

Figure 3:
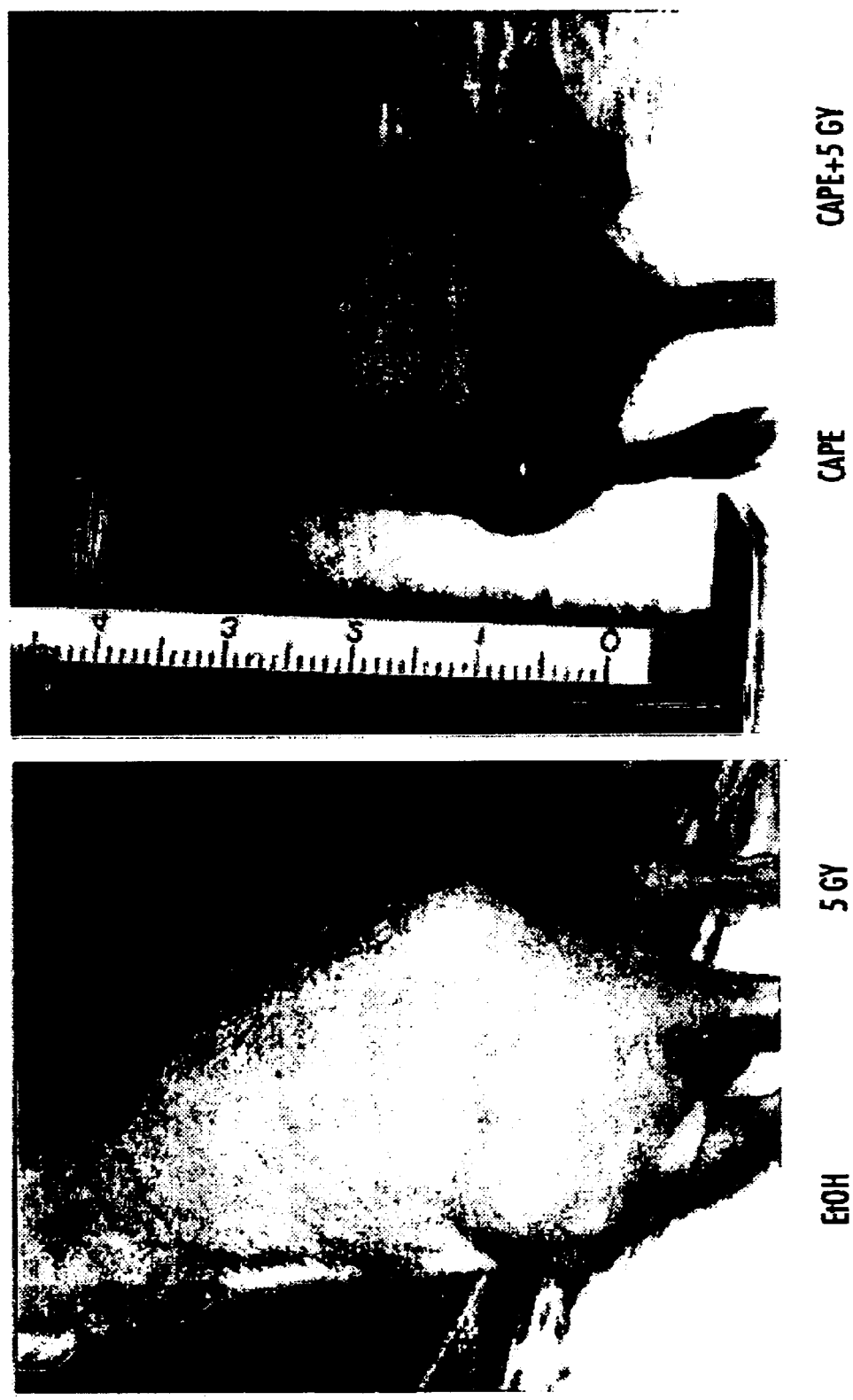
FIG. 3 is a photograph showing representative animals where CAPE radiosensitizes HT-29 xenograft tumors to IR. HT-29 cells were grown as tumor xenografts on the flanks of nude mice. When the tumors reached approximately 80 mm$^3$, one group of mice was treated with 0.5 ml of ethanol (EtOH) (0.1%) while the other group was treated with a single injection of CAPE (100 µg/kg). Twenty-four hours later, the tumors on the left flanks were given a single dose of IR (5 Gy). The animals were returned to their cages and tumor measurements were taken every 7 days for the following 4 weeks. The animal on the left was treated with ethanol (EtOH) (the carrier for CAPE), while the animal on the right was treated with 50 mg/kg CAPE. The tumors on the left side of the animal (right side of the picture) was treated with ionizing radiation (IR) (5Gy). Pictures were taken 4 weeks following IR.
Figure 4:
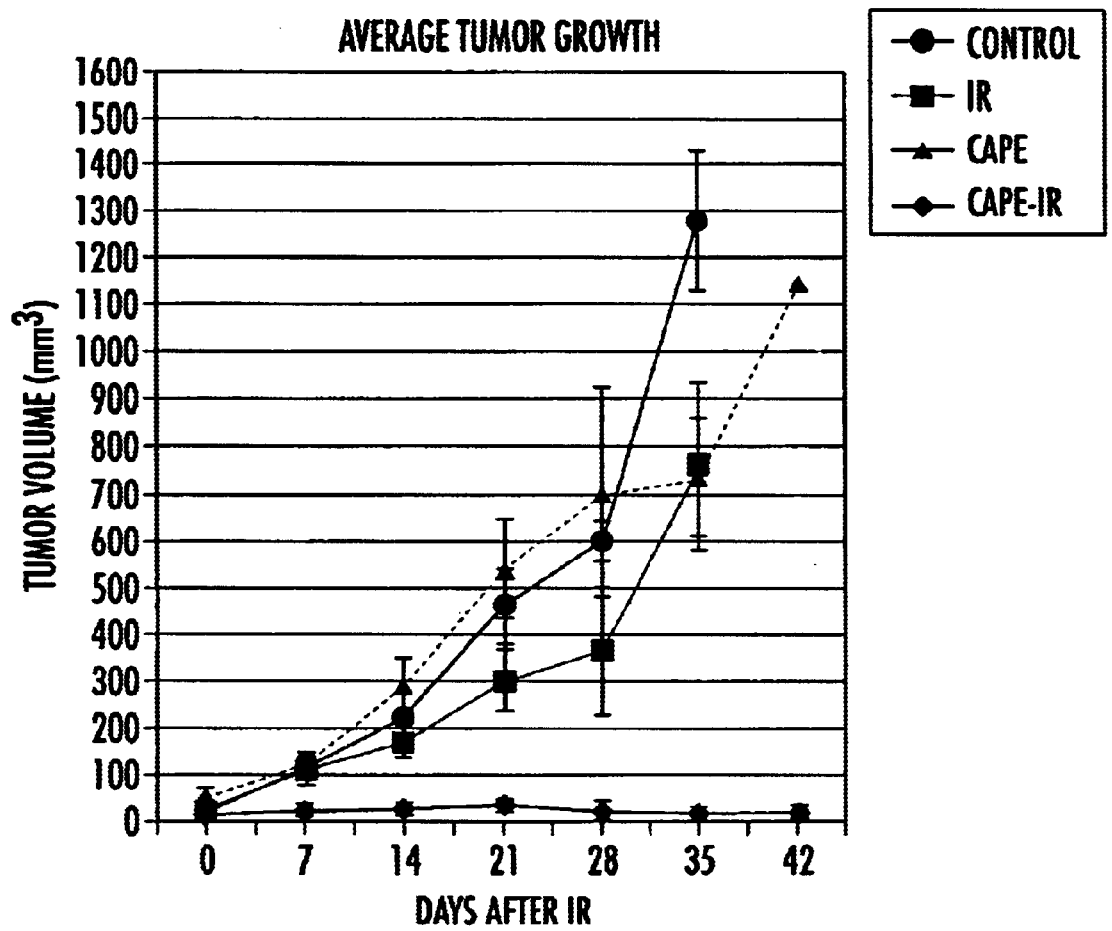
FIG. 4 is graphical representation of results from all tumors. Control (N=7), CAPE (N=5), IR (N=6) and CAPE +IR (N=4). Error bars represent ±S.E.M. The different number of tumors measured reflects the failure of some of the tumors to grow during the first week prior to treatment.
Figure 5:
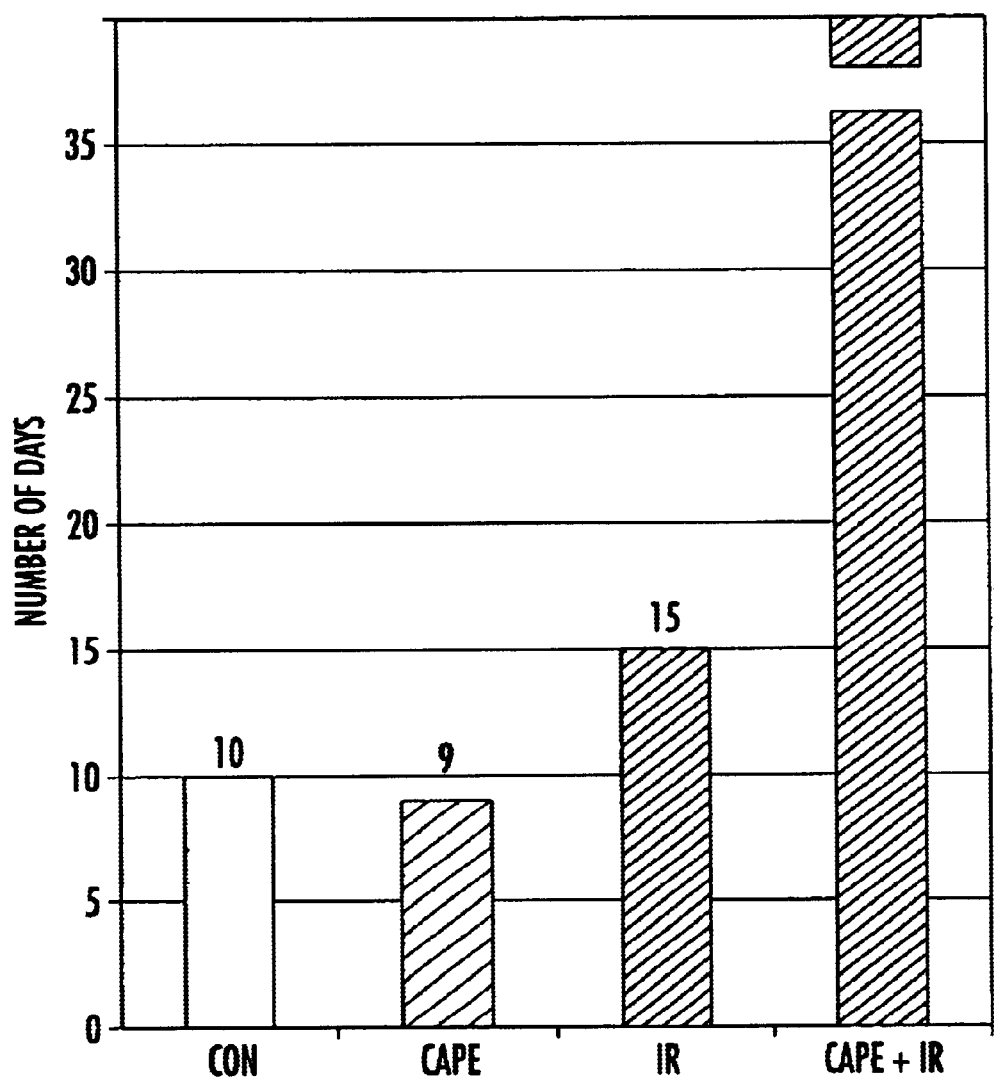
FIG. 5 is a bar graph illustrating the number of days required for a tumor to triple in volume.

As shown in the picture depicted in FIG. 3, at a single dose (50 mg/kg), CAPE had a minimal effect on tumor growth, while IR alone reduced the size of the tumors by an average of 50%. FIG. 4 illustrates that tumors treated with both CAPE and IR were reduced in size by approximately 90% 4 weeks after treatment. Additionally, FIG. 5 illustrates that the addition of CAPE to IR increased the number of days to an infinite period as the tumor failed to triple in volume when the two therapies were combined with one another. These results indicate that CAPE is a potent radiosensitizer in animal tumor xenografts.

EXAMPLE 4

Figure 6:
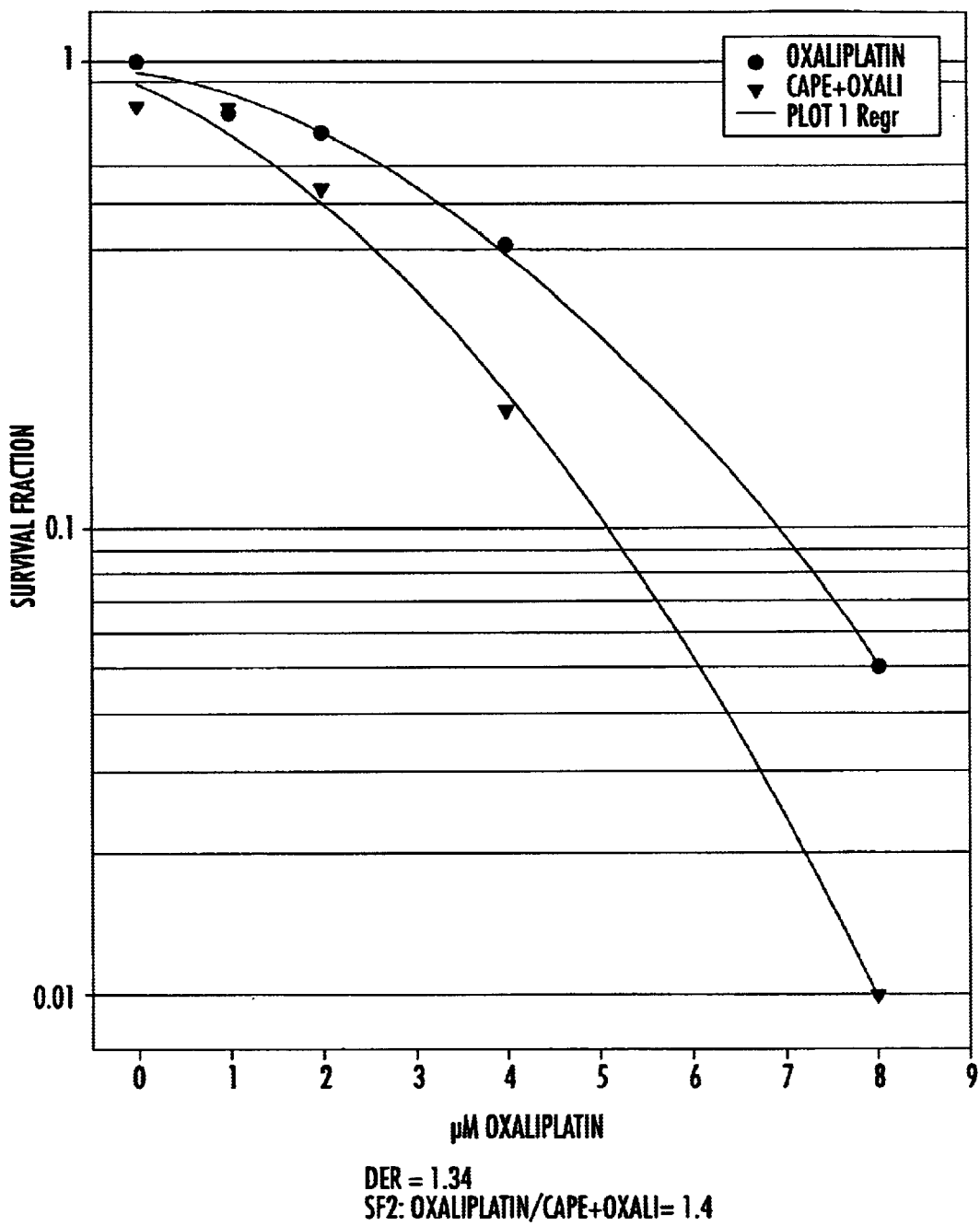
FIG. 6 is a graph depicting the survival fraction of colorectal carcinoma cells when the cells are given a regimen of oxaliplatin as compared to a regimen of CAPE and oxaliplatin.

As stated above, CAPE may be combined with other cancer therapies. One such therapy includes the use of oxaliplatin. Oxaliplatin is a chemotherapy drug, and also an antineoplastic agent, that is generally used in late-stage clinical development for colorectal cancer. Oxaliplatin is a platinum chemotherapy drug, similar to cisplatin and carboplatin. At the center of the drug molecule is an atom of platinum. Oxaliplatin is generally a clear liquid that is given through a drip into a vein (intravenous infusion). The infusion usually takes about 2 hours. Oxaliplatin can be given every 2 weeks or every 3 weeks as a course of treatment. FIG. 6 illustrates a decrease in the survival fraction of cancerous cells when a regimen using CAPE plus oxaliplatin is followed.

The foregoing is illustrative of the present invention, and is not to be construed as limiting thereof. The invention is defined by the following claims, with equivalents of the claims to be included therein.

What is claimed is:

1. A method of potentiating radiation therapy in a subject in need thereof, comprising administering a potentiating agent comprising caffeic acid phenethyl ester (CAPE) or an analog thereof to said subject in an amount effective to potentiate radiation therapy in said subject.

2. The method according to claim 1, wherein said patient is afflicted with a lung, breast, colon, prostate, liver, ovary, or brain tumor.

3. The method according to claim 1, wherein said patient is afflicted with a prostate tumor.

4. The method according to claim 1, wherein said patient is afflicted with an adenocarcinoma of the prostate at stage B2 or higher.

5. The method according to claim 1 wherein said potentiating agent comprises a compound of Formula I:

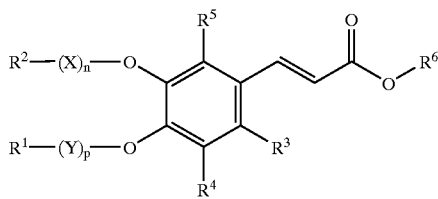

(I)

wherein:

X and Y are independently carbonyl, C=S, S=O, or O=S=O;

n and p are independently 0 or 1;

$R^1$ and $R^2$ are independently hydrogen, linear or branched $C_1$–$C_{18}$ alkyl, alkenyl, or alkynyl, either unsubstituted or substituted with halogen, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$ are independently hydrogen, halogen, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S) $R^{14}$, (S=O) $R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, $C_1$–$C_6$ alkoxy, (C=O)$R^{18}$, (C=O)O$R^{19}$, or aryl; wherein $R^{18}$ and $R^{19}$ are independently $C_1$–$C_6$ branched or linear alkyl;

or a pharmaceutically acceptable salt thereof.

6. The method according to claim 1, wherein said potentiating agent comprises caffeic acid phenethyl ester.

7. A method of treating a tumor in a subject, comprising concurrently administering (i) a potentiating agent comprising CAPE or an analog thereof to said subject and (ii) radiation therapy to said tumor, the potentiating agent being administered to said subject in an amount effective to potentiate said radiation therapy.

8. The method according to claim 7, wherein said radiation therapy comprises administering ionizing radiation to said tumor in an amount effective to reduce the mass of said tumor.

9. The method according to claim 7, wherein said patient is afflicted with a lung, breast, colon, prostate, liver, ovary, or brain tumor.

10. The method according to claim 7, wherein said patient is afflicted with a prostate tumor.

11. The method according to claim 7, wherein said patient is afflicted with an adenocarcinoma of the prostate at stage B2 or higher.

12. The method according to claim 7 wherein said potentiating agent comprises a compound of Formula I:

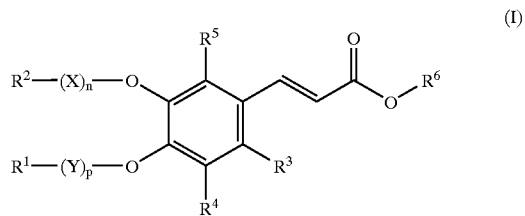

(I)

wherein:

X and Y are independently carbonyl, C=S, S=O, or O=S=O;

n and p are independently 0 or 1;

$R^1$ and $R^2$ are independently hydrogen, linear or branched $C_1$–$C_{18}$ alkyl, alkenyl, or alkynyl, either unsubstituted or substituted with halogen, $C_1$–$C_6$ alkoxy, (C=O)$R^7$, or (C=O)O$R^8$; wherein $R^7$ and $R^8$ are independently $C_1$–$C_6$ linear or branched alkyl;

$R^3$, $R^4$, and $R^5$ are independently hydrogen, halogen, trihalomethyl, $C_1$–$C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S) $R^{14}$, (S=O) $R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1$–$C_{18}$ linear or branched alkyl, alkenyl, or alkynyl; and $R^6$ is aryl or $C_1$–$C_{18}$ branched or linear alkyl, alkenyl, or alkynyl, either unsubstituted or substituted with halogen, $C_1$–$C_6$ alkoxy, (C=O)$R^{18}$, (C=O)O$R^{19}$, or aryl; wherein $R^{18}$ and $R^9$ are independently $C_1$–$C_6$ branched or linear alkyl;

or a pharmaceutically acceptable salt thereof.

13. The method according to claim 7, wherein said potentiating agent comprises caffeic acid phenethyl ester.

14. A composition for treating a tumor in a subject, comprising, in combination in a pharmaceutically acceptable carrier, (i) a potentiating agent comprising CAPE or an analog thereof, and (ii) a radiation therapy agent.

15. The composition according to claim 14 wherein said potentiating agent comprises a compound of Formula I:

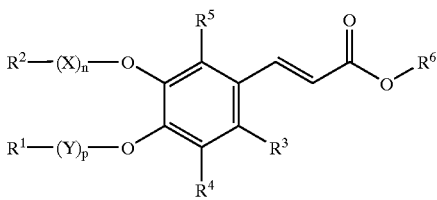

(I)

wherein:

X and Y are independently carbonyl, C=S, S=O, or O=S=O;

n and p are independently 0 or 1;

$R^1$ and $R^2$ are independently hydrogen, linear or branched $C_1-C_{18}$ alkyl, alkenyl, or alkynyl, either unsubstituted or substituted with halogen, $C_1-C_6$ alkoxy, (C=O)$R^7$, or (C=O)O$R^8$; wherein $R^7$ and $R^8$ are independently $C_1-C_6$ linear or branched alkyl;

$R^3$, $R^4$, and $R^5$ are independently hydrogen, halogen, trihalomethyl, $C_1-C_{18}$ linear or branched alkyl, alkenyl, alkynyl, haloalkyl, alkoxy, alkoxyalkyl, alkylthio, or (C=O)$R^9$, (C=O)O$R^{10}$, O(C=O)$R^{11}$, (C=S)$R^{12}$, (C=S)O$R^{13}$, O(C=S) $R^{14}$, (S=O) $R^{15}$, (S=O)O$R^{16}$, or (O=S=O)O$R^{17}$; wherein $R^9$, $R^{10}$, $R^{11}$, $R^{12}$, $R^{13}$, $R^{14}$, $R^{15}$, $R^{16}$, and $R^{17}$ are independently $C_1-C_{18}$ linear or branched alkyl, alkenyl, or alkynyl; and $R^6$ is aryl or $C_1-C_{18}$ branched or linear alkyl, alkenyl, or alkynyl, either unsubstituted or substituted with halogen, $C_1-C_6$ alkoxy, (C=O)$R^{18}$, (C=O)O$R^{19}$, or aryl; wherein $R^{18}$ and $R^{19}$ are independently $C_1-C_6$ branched or linear alkyl;

or a pharmaceutically acceptable salt thereof.

16. The composition according to claim 14, wherein said potentiating agent comprises caffeic acid phenethyl ester.

17. The composition according to claim 14, wherein said radiation therapy agent is selected from the group consisting of radioactive compounds and radiation sensitizing agents.

18. The composition according to claim 14, wherein said radiation therapy agent comprises a cancer cell receptor ligand.

19. The composition according to claim 14, wherein said radiation sensitizing agent is selected from the group consisting of implanted neural stem cells, taxols, texaphyrins and camptothecins.

* * * * *